(12) United States Patent
Eli et al.

(10) Patent No.: US 9,498,359 B2
(45) Date of Patent: *Nov. 22, 2016

(54) POLYMER SCAFFOLDS FOR PERIPHERAL VESSELS

(75) Inventors: Erik David Eli, Redwood City, CA (US); Michael Huy Ngo, San Jose, CA (US); Mikael Trollsas, San Jose, CA (US); Syed Hossainy, Hayward, CA (US); Joshua Takeshi Smith, Campbell, CA (US); Dariush Davalian, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 222 days.

This patent is subject to a terminal disclaimer.

(21) Appl. No.: 13/549,366

(22) Filed: Jul. 13, 2012

(65) Prior Publication Data

US 2014/0018903 A1 Jan. 16, 2014

(51) Int. Cl.
*A61F 2/915* (2013.01)

(52) U.S. Cl.
CPC ...... *A61F 2/915* (2013.01); *A61F 2002/91575* (2013.01); *A61F 2210/0004* (2013.01); *A61F 2230/0054* (2013.01)

(58) Field of Classification Search
CPC .... A61F 2/04; A61F 2/82; A61F 2002/9155; A61F 2002/91558; A61F 2002/91566; A61F 2002/91583; A61F 2/915; A61F 2002/91575; A61F 2230/0054; A61F 2210/0004
USPC ...................... 623/1.1, 1.12, 1.14, 1.15, 1.16
See application file for complete search history.

(56) References Cited

U.S. PATENT DOCUMENTS

| 5,925,061 | A | 7/1999 | Ogi et al. | |
|---|---|---|---|---|
| 6,231,598 | B1 | 5/2001 | Berry et al. | |
| 2001/0044652 | A1 | 11/2001 | Moore | |
| 2006/0076708 | A1* | 4/2006 | Huang et al. | 264/239 |
| 2006/0235505 | A1* | 10/2006 | Oepen et al. | 623/1.15 |
| 2006/0271170 | A1 | 11/2006 | Gale et al. | |
| 2007/0073384 | A1* | 3/2007 | Brown et al. | 623/1.16 |
| 2007/0282433 | A1 | 12/2007 | Limon et al. | |
| 2008/0065194 | A1 | 3/2008 | Dakin et al. | |
| 2008/0221661 | A1* | 9/2008 | Bidne et al. | 623/1.15 |
| 2008/0275537 | A1 | 11/2008 | Limon et al. | |

(Continued)

FOREIGN PATENT DOCUMENTS

| EP | 1 679 095 | 7/2006 |
|---|---|---|
| WO | WO 2007/146354 | 12/2007 |
| WO | 2010/151497 | 12/2010 |
| WO | WO 2011/094621 | 8/2011 |

OTHER PUBLICATIONS

U.S. Appl. No. 13/118,311, filed May 27, 2011, Liu et al.

(Continued)

*Primary Examiner* — Christopher D Prone
*Assistant Examiner* — Rokhaya Diop
(74) *Attorney, Agent, or Firm* — Squire Patton Boggs (US) LLP

(57) ABSTRACT

A medical device includes a polymer scaffold crimped to a catheter having an expansion balloon. The scaffold has a structure that produces a low late lumen loss when implanted within a peripheral vessel and also exhibits a high axial fatigue life. In a preferred embodiment the scaffold forms ring structures interconnected by links, where a ring has 12 crowns and at most two links connecting adjacent rings.

13 Claims, 17 Drawing Sheets

(56) References Cited

U.S. PATENT DOCUMENTS

| | | |
|---|---|---|
| 2009/0163989 A1* | 6/2009 | Contiliano et al. .......... 623/1.15 |
| 2010/0004734 A1 | 1/2010 | Ramzipoor et al. |
| 2010/0174309 A1* | 7/2010 | Fulkerson et al. ............ 606/200 |
| 2010/0217377 A1* | 8/2010 | Tsui .............................. 623/1.15 |
| 2010/0244329 A1 | 9/2010 | Hossainy et al. |
| 2011/0066222 A1 | 3/2011 | Wang et al. |
| 2011/0190871 A1 | 8/2011 | Trollsas et al. |
| 2012/0029618 A1* | 2/2012 | Tischler et al. .............. 623/1.16 |

OTHER PUBLICATIONS

International Search Report for PCT/US2011/023036, mailed May 12, 2011, 5 pgs.

International Search Report for PCT/US2012/029556, mailed Jul. 30, 2012, 5 pgs.

International Search Report for PCT/US2013/025975, mailed May 27, 2013, 5 pgs.

* cited by examiner

| Attribute | FIG.5A item | in | mm | other | v80 Comments |
|---|---|---|---|---|---|
| Total Length | — | 0.00 | | | Nominal for 40mm balloon, no Marker |
| Number of Rings | — | | | 17 | |
| Number of Links per Ring | — | | | 2 | Evenly distributed |
| Number of Crests per Ring | — | | | 12 | Internal Pattern: U U W U U Y U U W U U Y |
| Cut Tube OD | — | 0.276 | 7 | | |
| Wall Thickness | — | 0.011 | 0.279 | | |
| Strut Width | 363a | 0.008 | 0.200 | | |
| | | | | | |
| Link Width | 363b | 0.008 | 0.200 | | |
| Strut Length | 364 | 0.047 | 1.200 | | |
| Proximal Strut Length | | 0.052 | 1.322 | | Designed for similar theoretical max expansion as body |
| Angle (U) - deg | 368 | | | 81 | Angles based on 7mm tube |
| Angle (W) - deg | 367 | | | 81 | Angles based on 7mm tube |
| Angle (Y) - deg | 366 | | | 81 | Angles based on 7mm tube |
| | | | | 66 | |
| | | | | 66 | |
| Inner Radius (U) | 372 | 0.007 | 0.18 | | |
| Outer Radius (U) | 372 | 0.015 | 0.38 | | |
| Inner Radius (W) | 372 | 0.007 | 0.18 | | |
| Outer Radius (W) | 372 | 0.015 | 0.38 | | |
| Inner Radius (Y) | 372 | 0.007 | 0.18 | | |
| Outer Radius (Y) | 372 | 0.015 | 0.38 | | |

FIG. 6A

| Attribute | FIG.5B | v76 | | |
|---|---|---|---|---|
| | item | in | mm | other |
| Total Length | — | 1.44 | 36.5 | |
| Number of Rings | — | | | 17 |
| Number of Links per Ring | — | | | 2 |
| Number of Crests per Ring | — | | | 8 |
| Cut Tube OD | — | 0.28 | 7 | |
| Wall Thickness | — | 0.011 | 0.279 | |
| Strut Width | 263a | 0.012 | 0.300 | |
| | | | | |
| Link Width | 263b | 0.008 | 0.200 | |
| Strut Length | 264 | 0.069 | 1.740 | |
| | | | | |
| Angle (U) - deg | 268 | | | 81 |
| Angle (W) - deg | 267 | | | 81 |
| Angle (Y) - deg | 266 | | | 81 |
| | | | | |
| Inner Radius (U) | 272 | 0.0071 | 0.18 | |
| Outer Radius (U) | 273 | 0.019 | 0.48 | |
| Inner Radius (W) | 272 | 0.0071 | 0.18 | |
| Outer Radius (W) | 273 | 0.019 | 0.48 | |
| Inner Radius (Y) | 272 | 0.0071 | 0.18 | |
| Outer Radius (Y) | 273 | 0.019 | 0.48 | |

FIG. 6B

| 7% Compression 80,000 cycles @ 1 Hz (1 month) | Axial Compression Tester (Santa Clara) | | |
|---|---|---|---|
| | Fracture @ Crown | Fracture @ Connector Link | Total Fracture |
| V76 (6 x 60 mm) N=5 | 0 ± 0 | 0 ± 0 | 0 ± 0 |

| 7% Compression 500,000 cycles @ 1 Hz (6 months) | Axial Compression Tester (Santa Clara) | | |
|---|---|---|---|
| | Fracture @ Crown | Fracture @ Connector Link | Total Fracture |
| V76 (6 x 60 mm) N=5 | 2.4 ± 2.30 | 2.2 ± 1.92 | 4.6 ± 2.19 |

| Design | Acute Recoil % |
|--------|----------------|
| V59 | 3.2 ± 0.6% |
| V62 | 3.8 ± 0.6% |
| V2 | 2.5 ± 0.5% |
| V76 | 3.3 ± 0.6% |

POLYMER SCAFFOLDS FOR PERIPHERAL VESSELS

FIELD OF THE INVENTION

The present invention relates to drug-eluting medical devices; more particularly, this invention relates to polymeric scaffolds that are expanded by a delivery balloon.

BACKGROUND OF THE INVENTION

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen (one example of a stent is found in U.S. Pat. No. 6,066,167 to Lau et al). Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

The stent must be able to satisfy a number of basic, functional requirements. The stent must be capable of withstanding the structural loads, for example, radial compressive forces, imposed on the stent as it supports the walls of a vessel after deployment. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Even before the radial yield strength is exceeded there may be permanent deformation in the stent a following radial compressive load, but this degree of permanent deformation somewhere in the stent is not severe enough to have a significant effect on the stent's overall ability to radially support a vessel. Therefore, in some cases the art may view "radial yield strength" as the maximum radial loading, beyond which the scaffold stiffness changes dramatically. "Radial yield strength" units are sometimes force-divided-by-length, which is an expression of radial yield strength on a per-unit-length basis. Thus, for a radial yield strength per unit length, e.g., F N/mm, the radial load which, if it exceeds this value, would result in significant change in stiffness for a stent having two different lengths, L1 and L2, would therefore be the product F*L1 and F*L2, respectively. The value F, however, is the same in both cases, so that a convenient expression can be used to appreciate the radial yield strength independent of the length of the stent. Typically, the radial force that identifies the point where stiffness is lost does not change much on a per-unit-length basis when the stent length changes.

A commonly used type of peripheral stent is the self-expanding stent made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. Complications resulting from COF are discussed in Schwartz, Lewis B. et al. *Does Stent Placement have a learning curve: what mistakes do we as operators have to make and how can they be avoided?*, Abbott Laboratories; Abbott Park, Ill., USA. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF. Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel.

A balloon-expanded polymer scaffold, such as that described in US 2010/0004735 is made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. The polymer scaffold described in US 2010/0004735, as opposed to a metal stent, is intended to remain in the body for only a limited period of time. The scaffold is made from a biodegradable or bioerodable polymer. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a polymer scaffold.

The art recognizes a variety of factors that affect a polymeric scaffold's ability to retain its structural integrity and/or shape when subjected to external loadings, such as crimping and balloon expansion forces. These interactions are complex and the mechanisms of action not fully understood. According to the art, characteristics differentiating a polymeric, bio-absorbable scaffold of the type expanded to a deployed state by plastic deformation from a similarly functioning metal scaffold are many and significant. Indeed, several of the accepted analytic or empirical methods/models used to predict the behavior of metallic scaffolds tend to be unreliable, if not inappropriate, as methods/models for reliably and consistently predicting the highly non-linear, time dependent behavior of a polymeric load-bearing structure of a balloon-expandable scaffold. The models are not generally capable of providing an acceptable degree of certainty required for purposes of implanting the scaffold within a body, or predicting/anticipating the empirical data.

Polymer material considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material, only compound this complexity in working with a polymer, particularly, bio-absorbable polymer such as PLLA or PLGA.

Processing steps performed on, and design changes made to a metal stent that have not typically raised concerns for, or required careful attention to unanticipated changes in the average mechanical properties of the material, therefore, may not also apply to a polymer scaffold due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after scaffold fabrication, e.g., crimping? As a consequence, a change to a fabrication process, post-fabrication process or even relatively minor changes to a scaffold pattern design must, generally speaking, be investigated more thoroughly than if a metallic material were used instead of the polymer. It follows, therefore, that when choosing among different polymeric scaffold designs for improvement thereof, there are far less inferences, theories, or systematic methods of discovery available, as a tool for steering one clear of unproductive paths, and towards more productive paths for improvement, than when making changes in a metal stent.

The present inventors recognize, therefore, that, whereas inferences previously accepted in the art for stent validation or feasibility when an isotropic and ductile metallic material was used, those inferences would be inappropriate for a polymeric scaffold. A change in a polymeric scaffold pattern may affect not only the stiffness or lumen coverage of the scaffold in its deployed state supporting a lumen, but also the propensity for fractures to develop when the scaffold is crimped or being deployed. This means that, in comparison to a metallic stent, there is generally no assumption that can be made as to whether a changed scaffold pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a polymeric scaffold that is plastically deformed, both when crimped to, and when later deployed by a balloon, unfortunately, is not predictable to the same or similar degree as for a metal stent. Indeed, it is recognized that unexpected problems may arise in polymer scaffold fabrication steps as a result of a changed pattern that would not have necessitated any changes if the pattern was instead formed from a metal tube. In contrast to changes in a metallic stent pattern, a change in polymer scaffold pattern may necessitate other modifications in fabrication steps or post-fabrication processing, such as crimping and sterilization.

Scaffolds used to treat coronary vessels experience, for the most part, a primarily radial loading. However, scaffolds intended for peripheral vessels experience a quite different loading, to such an extent that the traditional measure of a stent's fitness for use, i.e., its radial strength/stiffness, is not an accurate measure of whether the scaffold will have sufficient strength to provide mechanical support within the peripheral vessel for the duration needed. This is because a peripheral scaffold is placed in a significantly different environment from a coronary scaffold. The vessel size is larger. And there is much more movement of the vessel, especially when located close to an appendage. As such, a scaffold intended for a peripheral vessel will need to be able to sustain more complex loading, including a combination of axial, bending, torsional and radial loading. See e.g. Bosiers, M. and Schwartz, L., *Development of Bioresorbable Scaffolds for the Superficial Femoral Artery*, SFA: CONTEMPORARY ENDOVASCULAR MANAGEMENT ('Interventions in the SFA" section). These and related challenges facing peripherally implanted stents and scaffolds are also discussed in U.S. application Ser. No. 13/015,474.

There is a need to develop a prosthesis for treating peripheral blood vessels that can maintain its structural integrity for a period of time long enough to provide a mechanical support for the vessel, until this support is no longer needed. There is a further need to develop such a prosthesis that minimizes late lumen loss and stenosis of the vessel, such as within the first month following implantation, thereby providing improved vascular patency.

SUMMARY OF THE INVENTION

In response to these needs there is provided a peripherally-implantable and bio-erodible polymer scaffold that has a lower fracture rate, discontinuity or percentage of fractured structure. The scaffold is capable of maintaining its scaffolding support of a vessel wall sufficiently for up to about a 1, 2, and 3 month period following implantation, following which the scaffolding begins to degrade as it should no longer be needed to maintain vascular patency. Surprisingly and unexpectedly, the polymer scaffold according to one embodiment is capable of producing a significantly lower late lumen loss than prior scaffold designs about 28 days after implantation.

According to one aspect of the invention, there is a balloon-expandable scaffold forming ring structures. Each ring is connected to adjacent rings by no more than two links and each ring has at least 8 crests and 8 troughs, and preferably 12 crests and 12 troughs formed by strut elements. The high number of crowns in the preferred embodiment is believed to provide a higher density of strut elements to support the vessel such that the surface area provided to support the vessel increases over a scaffold having fewer crowns. Additionally, for the same number of cracks or fractures occurring in the scaffold (as compared to a scaffold having fewer crowns) the overall percentage of cracks at crowns is reduced. It is believed that this combination of increased supporting surface area for the vessel walls and lower percentage of cracked to un-cracked or functional crowns is a significant factor contributing to a reduction in late lumen loss and reduced stenosis of the vessel.

According to another aspect of the invention, a scaffold provides a desired vascular patency by increasing the surface area coverage of a scaffold at the expense of reducing the radial strength of the scaffold. In one example, a scaffold pattern is characterized by a reduced strut length and increased number of crowns for ring structures. For this scaffold an equal number of fractures as a more radial-stiff scaffold produces a lower percentage of functioning-to-nonfunctioning crown-strut structures due to a higher number of such structures as compared to the more radial stiff scaffold.

According to another aspect of the invention, there is provided a scaffold having at most two links connecting adjacent ring structure and with or without an increased number of crowns to extend the scaffold's fatigue life during the period of time when the scaffold is needed to provide mechanical support to the vessel, e.g., during the first about one, two or three months following implantation. Tests have revealed that for a peripherally-implanted scaffold, particularly for scaffold located within arteries of appendages, failure in the scaffold structure has most often occurred due to repeated axial compression/extension and bending. Although the scaffold is in general subjected to a complex and time-varying combination of radial, axial, bending and torsion loads, it has been found that prior scaffold designs have been mostly susceptible to crack formation due to repeated cyclic axial and bending loads, e.g., 500,000 cycles of 7% axial compression/extension, which is considered equivalent to walking over a six month period. Repeated impacts between ring structures, longitudinal buckling (bending) of links or other behavior that may result from a reduction of axial and bending stiffness were not found to have a significant negative impact on vessel support or scaffold integrity based on in-vivo studies.

As an example of bending-induced fractures, an earlier design—the V59, which is described in WO2011094621—showed by comparison many more fractures during bending fatigue tests (90 degree bending at 1 Hz under water at 37 Deg. Celsius) up 1.7 million cycles. The cause for these failures was the scaffold being too stiff in bending, or its fracture toughness in bending not adequate for the test loading environment. The V59 has four links connecting adjacent ring structures. When a two link design is used, e.g., the V76 or V80, the same testing revealed substantially less fractures.

Again, the actual in-vivo loading environment is quite complex, involving axial, bending, torsion and radial loads. However, it was revealed through separate bending and axial loading bench tests for a four link verses a two link design compared to in-vivo data that when both bending and axial loading induced fractures were reduced in the bench tests, the fracture count of explanted scaffolds was also reduced significantly for the two verses four link scaffolds. This indicates that it is not so much the radial loading, but other loading not typically associated with critical stent mechanical functioning that is a key driver for balloon-expandable and peripherally-implantable scaffold design.

According to one embodiment, a peripherally-implanted medical device includes a balloon-expanded scaffold formed from a radially expanded polymer tube, the scaffold forming a network of rings interconnected by links, including at least 8 crests and 8 troughs, or 12 crests and 12 troughs per ring, and at most 2 links connecting substantially all pairs of adjacent rings, wherein for any ring of the scaffold there are an equal number of unsupported crowns on each side of each crown connected to a link. The two links allows the structure to better absorb/distribute stresses induced during combined axial loading and bending. Moreover, it was found that the structure's overall fatigue life is significantly increased when two links are used. Additionally, symmetry of the crowns or crests about a link helps to more equally distribute stresses, or reduce stress concentrations near crowns to improve fatigue life during axial loading and bending.

According to another aspect of invention, there is a method of treating a peripheral vessel including implanting a polymer scaffold at the vessel site, the scaffold having a network of rings interconnected by links, including 12 crests and 12 troughs per ring, and at most 2 links connecting substantially all pairs of adjacent rings, wherein the scaffold produces a substantially reduced late lumen loss after 28 days. For example the late lumen loss is about 0.4 mm or less than 1 mm for a 5-6 mm average vessel size. Clinically this is expected to result in in-stent late loss of at most 0.5 mm at 6-9 months in the SFA, compared to about 0.4-0.6 mm for the sirolimus eluting SMART stent or >1.0 mm for bare metal stents.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIGS. 6A and 6B are tables showing examples of scaffold features in accordance with aspects of the disclosure.

DETAILED DESCRIPTION OF EMBODIMENTS

Figure 1:
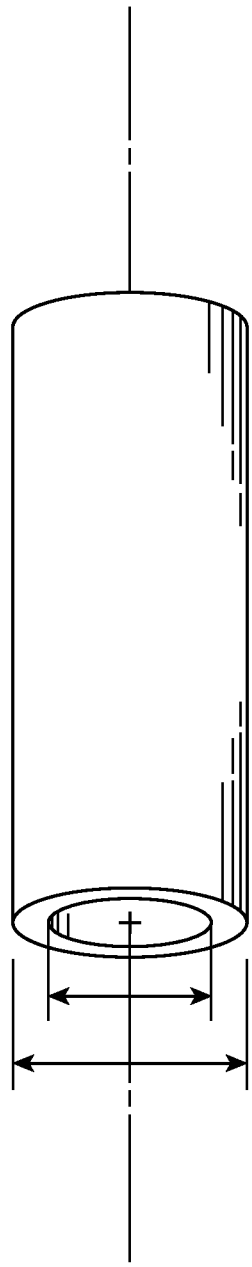
FIG. 1 is a perspective view of a deformed polymer tube. The tube is formed into a scaffold.

The disclosure proceeds as follows. First, definitions of terms that may be used during the course of the subsequent disclosure are explained. Embodiments of processes for forming a deformed polymer tube from a precursor are provided. According to the disclosure, the crush recoverable and balloon expandable scaffold is cut from a tube (FIG. 1) formed through a process intended to enhance mechanical properties of the scaffold including fracture toughness. Discussion of the scaffold patterns according to several embodiments are discussed next. Examples of the scaffold patterns are provided. During this discussion, reference is made to aspects of a scaffold found to play an important role in the stiffness, strength, crimping and deployment of a polymer scaffold. Finally, bench and in-vivo test results are discussed, including exemplary examples of embodiments of invention and explanation of the results observed and problems overcome. In these examples there may be gained a further appreciation of aspects of invention—a balloon-expandable polymer scaffold having increased flexibility and lower fracture rates or percentage in peripheral arteries, and a lower late lumen loss.

For purposes of this disclosure, the following terms and definitions apply:

"Reference vessel diameter" (RVD) is the diameter of a vessel in areas adjacent to a diseased section of a vessel that appear either normal or only minimally diseased.

"Minimal lumen diameter" (MLD) is the diameter of a diseased section of a vessel at the site of maximal reduction in the diameter.

% "Diameter restenosis" (% DS) is the percent difference between the reference vessel diameter and the minimal lumen diameter: (RVD−MLD)/RVD "Acute gain" is defined as the difference between pre- and post-procedural minimal lumen diameter.

"Late loss" is defined as the difference between minimal luminal diameter after the procedure or post-percutaneous coronary intervention (PCI) and minimal luminal diameter at follow-up.

"Acute Recoil" is defined as the percentage decrease in scaffold diameter within the first about ½ hour following implantation within a vessel.

"Inflated diameter" or "expanded diameter" refers to the maximum diameter the scaffold attains when its supporting balloon is inflated to expand the scaffold from its crimped configuration to implant the scaffold within a vessel. The inflated diameter may refer to a post-dilation diameter which is beyond the nominal balloon diameter, e.g., a 6.5 mm semi-compliant PEBAX balloon has about a 7.4 mm post-dilation diameter. The scaffold diameter, after attaining its inflated diameter by balloon pressure, will to some degree decrease in diameter due to recoil effects and/or compressive forces imposed by the wall of the vessel after the balloon is removed.

The glass transition temperature (referred to herein as "Tg") is the temperature at which the amorphous domains of a polymer change from a brittle vitreous state to a solid deformable or ductile state at atmospheric pressure. In other words, Tg corresponds to the temperature where the onset of segmental motion in the chains of the polymer occurs. Tg of a given polymer can be dependent on the heating rate and can be influenced by the thermal history of the polymer. Furthermore, the chemical structure of the polymer heavily influences the glass transition by affecting mobility of polymer chains.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e radial strength.

The term "crush recovery" is used to describe how the scaffold recovers from a pinch or crush load, while the term "crush resistance" is used to describe the force required to cause a permanent deformation of a scaffold. A scaffold or stent that does not possess good crush recovery does not substantially return to its original diameter following removal of a crushing force. As noted earlier, a scaffold or stent having a desired radial force can have an unacceptable crush recovery. And a scaffold or stent having a desired crush recovery can have an unacceptable radial force. Crush recovery and crush resistance aspects of scaffolds is described in greater detail in US20110190871.

Figure 2:
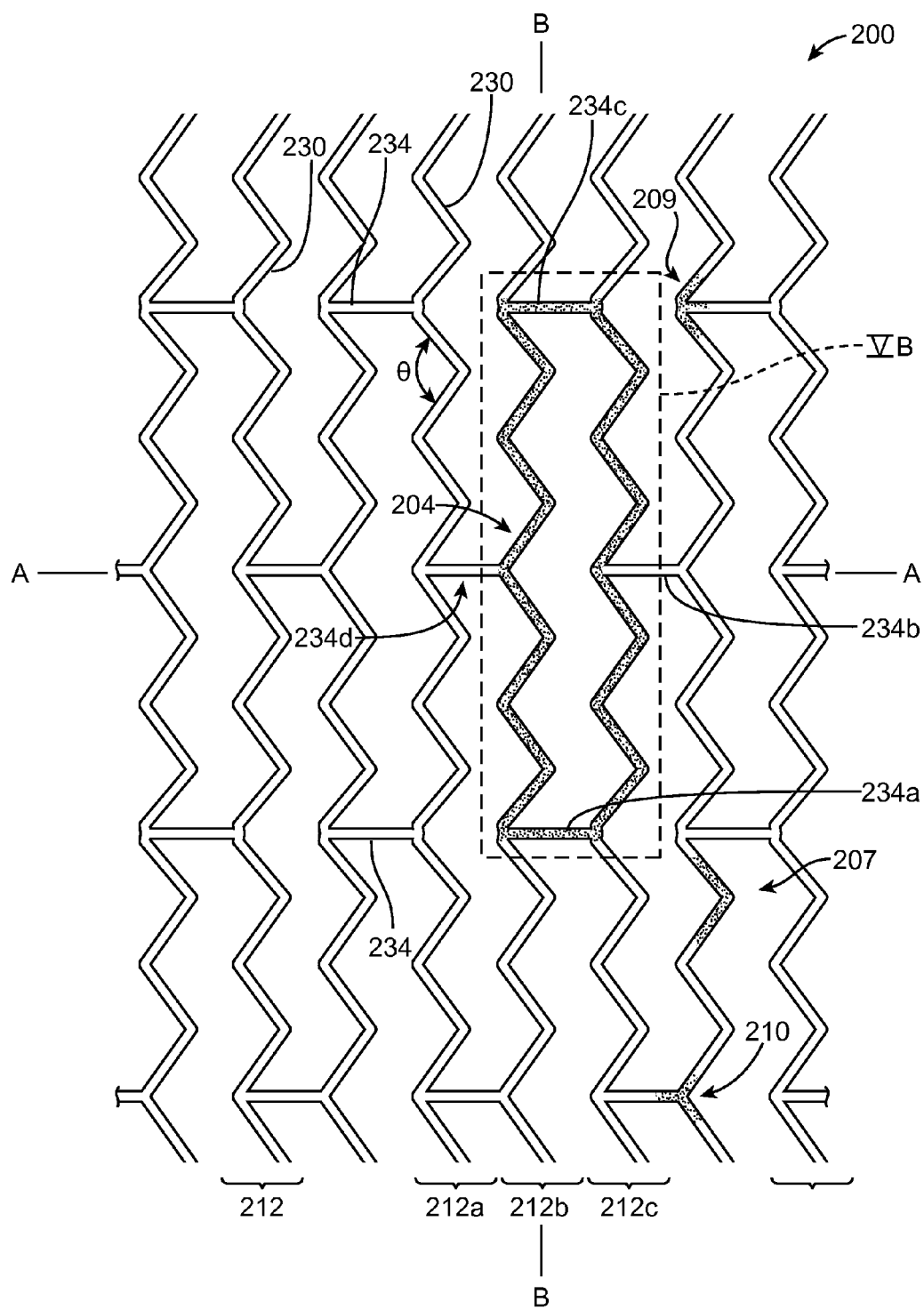
FIG. 2 is a partial planar view of a scaffold pattern according to a first embodiment of a scaffold.

The polymer scaffold illustrated in FIG. 2 is formed from a poly(L-lactide) ("PLLA") tube. The process for forming this PLLA tube may be the process described in U.S. patent application Ser. No. 12/558,105. Reference is made to a precursor that is "deformed" in order to produce the tube of FIG. 1 having the desired scaffold diameter, thickness and material properties as set forth below. Before the tube is deformed or, in some embodiments, expanded to produce the desired properties in the starting tube for the scaffold, the precursor is formed. The precursor may be formed by an extrusion process which starts with raw PLLA resin material heated above the melt temperature of the polymer which is then extruded through a die. Then, in one example, an expansion process for forming an expanded PLLA tube includes heating a PLLA precursor above the PLLA glass transition temperature (i.e., 60-70 degrees C.) but below the melt temperature (165-175 degrees C.), e.g., around 110-120 degrees C.

A precursor tube is deformed in radial and axial directions by a blow molding process wherein deformation occurs progressively at a predetermined longitudinal speed along the longitudinal axis of the tube. As explained below, the deformation improves the mechanical properties of the tube before it is formed into the scaffold of FIG. 2. The tube deformation process is intended to orient polymer chains in radial and/or biaxial directions. The orientation or deformation causing re-alignment is performed according to a precise selection of processing parameters, e.g. pressure, heat (i.e., temperature), deformation rate, to affect material crystallinity and type of crystalline formation during the deformation process.

In an alternative embodiment the tube may be made of poly(L-lactide-co-glycolide), poly(D-lactide-co-glycolide) ("PLGA"), polycaprolactone, ("PCL"), any semi-crystalline copolymers combining any of these monomers, or any blends of these polymers. Material choices for the scaffold should take into consideration the complex loading environment associated with many peripheral vessel locations, particularly those located close to limbs. Examples are described in U.S. patent application Ser. No. 13/525,145.

The femoral artery provides a dynamic environment for vascular implants as various forces may crush, twist, extend, or shorten the device simultaneously. The force application may vary between point load to distributed load or a combination thereof and also as a function of time. Recent results have shown that bioresorbable scaffolds made from highly crystalline PLLA can provide crush recovery without causing a permanent and constant outward radial force on the vessel. The permanent and constant outward radial force may be the cause of late clinical issues with nitinol self-expandable stents. However, a remaining challenge with bioresorbable scaffolds is to make them optimally fracture resistant as a function of time; that is, to improve their fatigue life or survivability under a variety of dynamic loading environments. There is a continuing need to improve fracture toughness for a scaffold; and in particular a peripherally implanted scaffold.

The fracture resistance of a vascular scaffold depends not only on the design and the material, but is also the manufacturing process and deployment parameters. Therefore it is in particular necessary to have a process, design, and a delivery system that allows the scaffold to be uniformly expanded and deployed. As a consequence of non-uniform deployment the various struts and crowns of a scaffold will potentially be exposed to very different forces and motions, which has a deleterious effect on the fatigue life.

Alternative ways to improve the fatigue properties are through introduction of axial flexibility and the use of pre-designed fracture points, in particular in the connector links. The fracture points could function as precursors of actual fractures, e.g., crazes and cracks or small dimension of fracture distributed in the implant. A distribution or pattern of cracks or crazes may dictate or inform one of an expected toughness of the scaffold when subjected to a particular loading, e.g., torsion, radial force, tensile etc. Although it is understand that, due to the generally highly non-linear relationship between crack formation and a coupled loading environment, that is, simultaneously applied and time varying bending, torsion and axial loading, such predictive methods may not be applicable to all situations.

Alternative ways to improve the fatigue properties are through introduction of axial flexibility and the use of pre-designed fracture points, in particular, fracture points in or near connector links as discussed in greater detail below.

For a tube of FIG. 1 having a diameter about 7 mm and a wall thickness above 200 micro-meters and more specifically a diameter of 8 mm and a wall thickness of 280 micro-meters, the temperature at expansion is 235+/−5 degrees Fahrenheit, the expansion pressure is 110+/−10 psi and the expansion speed is 0.68+/−0.20 mm/sec.

The degree of radial expansion that the polymer tube undergoes can partially characterize the degree of induced circumferential molecular and crystal orientation as well as strength in a circumferential direction. The degree of radial expansion is quantified by a radial expansion ("RE") ratio, defined as RE Ratio=(Inside Diameter of Expanded Tube)/(Original Inside Diameter of the tube). The RE ratio can also be expressed as a percentage, defined as RE %=(RE ratio-1).times.100%. The degree of axial extension that the polymer tube undergoes can partially characterize induced axial molecular or crystal orientation as well as strength in an axial direction. The degree of axial extension is quantified by an axial extension ("AE") ratio, defined as AE Ratio=(Length of Extended Tube)/(Original Length of the Tube). The AE ratio can also be expressed as a percentage, defined as AE %=(AE ratio-1).times.100%. In a preferred embodiment the RE is about 400% and the AE is 40-50%.

Figure 3:
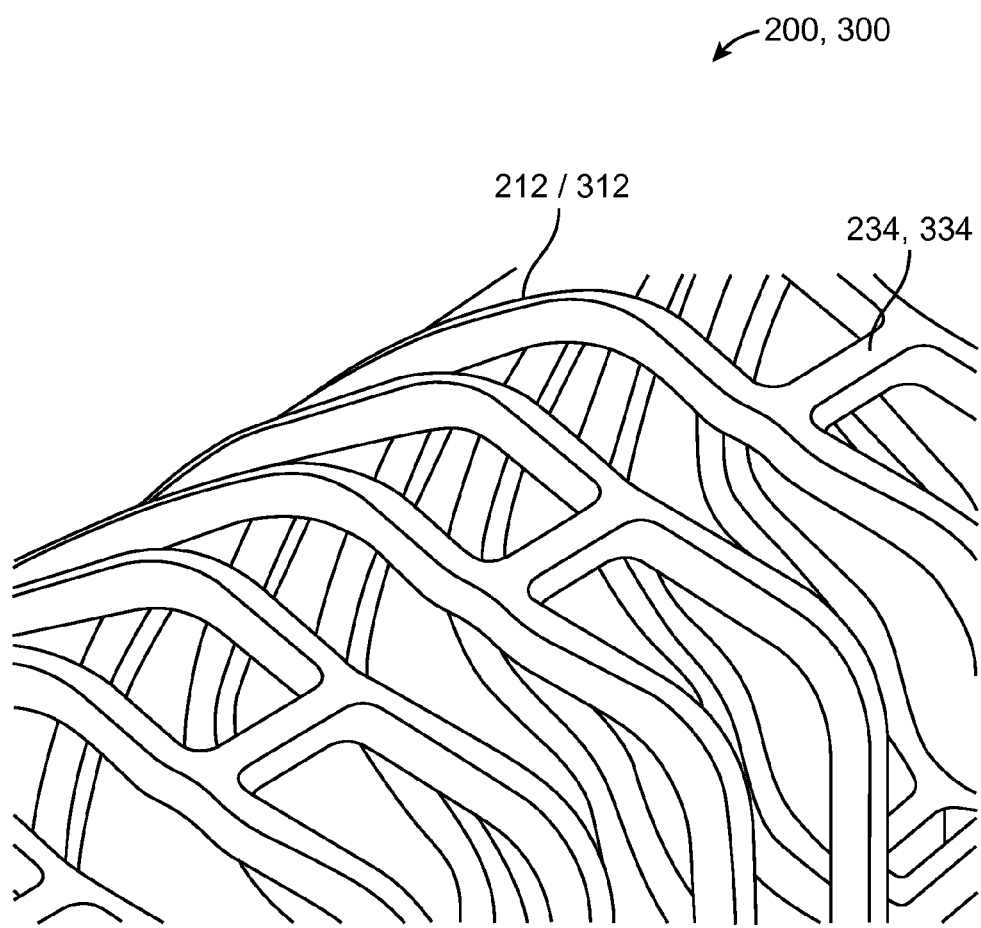
FIG. 3 is a partial perspective view of a scaffold structure.

The strengthened and toughened cylindrical, polymer tube of FIG. 1 is formed into a scaffold structure, in one embodiment a structure having a plurality of struts 230 and links 234 forming a pattern 200 as shown in FIG. 2 (pattern 200 is illustrated in a planar or flattened view), which is about the pattern for the scaffold before crimping and after the scaffold is plastically, or irreversibly deformed from its crimped state to its deployed state within a vessel by balloon expansion. The pattern 200 of FIG. 2, therefore, represents a tubular scaffold structure (as partially shown in three dimensional space in FIG. 3), so that an axis A-A is parallel to the central or longitudinal axis of the scaffold. FIG. 3 shows the scaffold in a state prior to crimping or after deployment. As can be seen from FIG. 3, the scaffold comprises a framework of struts and links that define a generally tubular body. The cylindrical, deformed tube of FIG. 1 may be formed into this open framework of struts and links described in FIGS. 2-3 by a laser cutting device, preferably, a pico-second green light laser that uses Helium gas as a coolant during cutting.

Referring to FIG. 2, the pattern 200 includes longitudinally-spaced rings 212 formed by struts 230. There are eight crests and eight troughs formed by the struts. A ring 212 is connected to an adjacent ring by no more than two links 234, each of which extends parallel to axis A-A. In this first embodiment of a scaffold pattern (pattern 200) two links 234 connect the interior ring 212, which refers to a ring having a ring to its left and right in FIG. 2, to each of the two adjacent rings. Thus, ring 212b is connected by two links 234 to ring 212c and two links 234 to ring 212a. An end ring (not shown) is an end ring connected to only one other ring.

A ring 212 is formed by struts 230 connected at crowns 207, 209 and 210. A link 234 is joined with struts 230 at a crown 209 (W-crown) and at a crown 210 (Y-crown). A crown 207 (free-crown) does not have a link 234 connected to it. Preferably the struts 230 that extend from a crown 207, 209 and 210 at a constant angle from the crown center, i.e., the rings 212 are approximately zig-zag in shape, as opposed to sinusoidal for pattern 200. As such, in this embodiment a ring 212 height, which is the longitudinal distance between adjacent crowns 207 and 209/210 may be derived from the lengths of the two struts 230 connecting at the crown and a crown angle θ. In some embodiments the angle θ at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 2). The struts 212 centroidal axes lie primarily at about the same radial distance from the scaffold's longitudinal axis. Ideally, substantially all relative movement among struts forming rings also occurs axially, but not radially, during crimping and deployment. Although, as explained in greater detail, below, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the axially and radially expanded tube from which the scaffold is cut) is always greater than, or equal to a maximum expanded scaffold diameter that the delivery balloon can, or is capable of producing when inflated.

Figure 4:
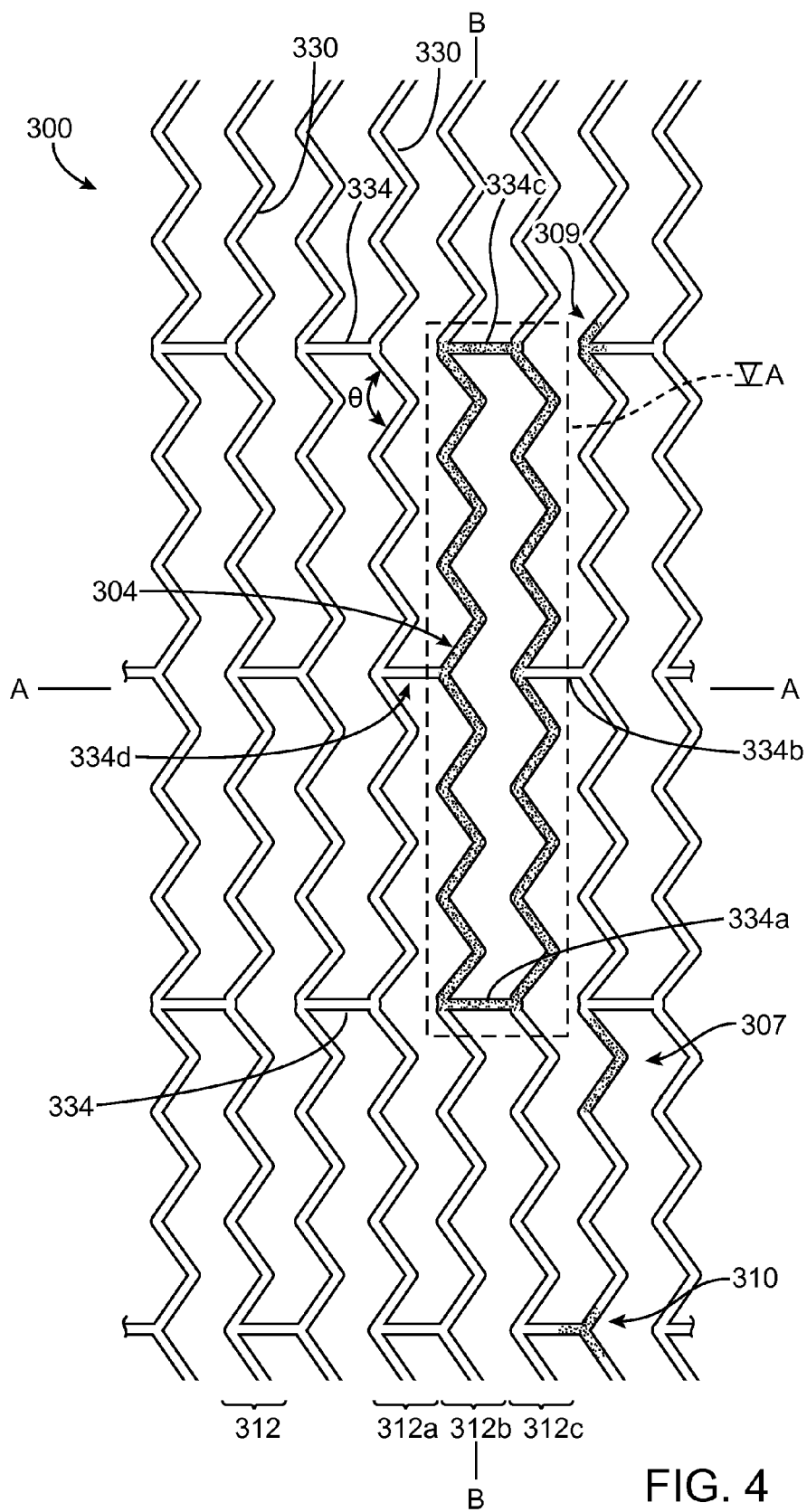
FIG. 4 is a partial planar view of a scaffold pattern according to a second embodiment of a scaffold.

A second embodiment of a scaffold structure has the pattern 300 illustrated in FIG. 4. Like the pattern 200, the pattern 300 includes longitudinally-spaced rings 312 formed by struts 330. There are twelve crests and twelve troughs formed by the struts for each ring 312. A ring 312 is connected to an adjacent ring by no more than two links 334, each of which extends parallel to axis A-A. The description of the structure associated with rings 212, struts 230, links 234, and crowns 207, 209, 210 in connection with FIG. 2, above, also applies to the respective rings 312, struts 330, links 334 and crowns 307, 309 and 310 of the second embodiment, except that in the second embodiment there are 12, as opposed to 8 crests for each ring 312 for pattern 300.

Figure 5A:
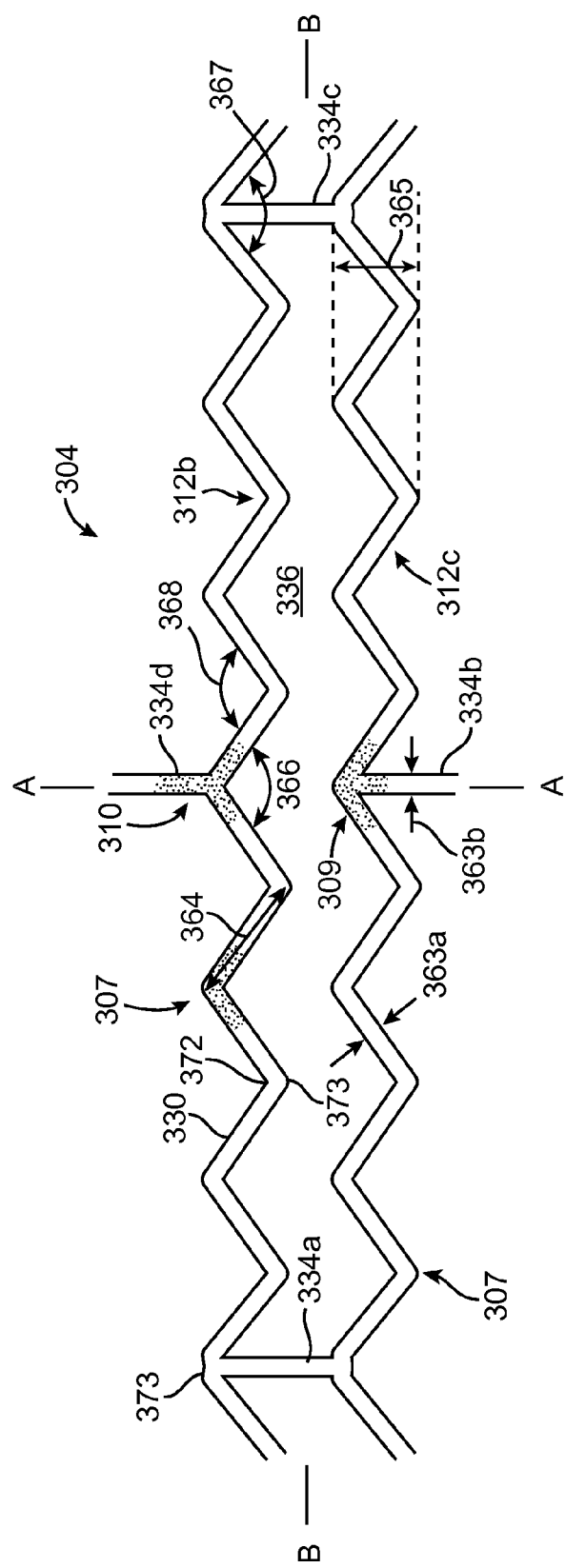
FIG. 5A shows the portion VA of the scaffold pattern of FIG. 4.
Figure 5B:
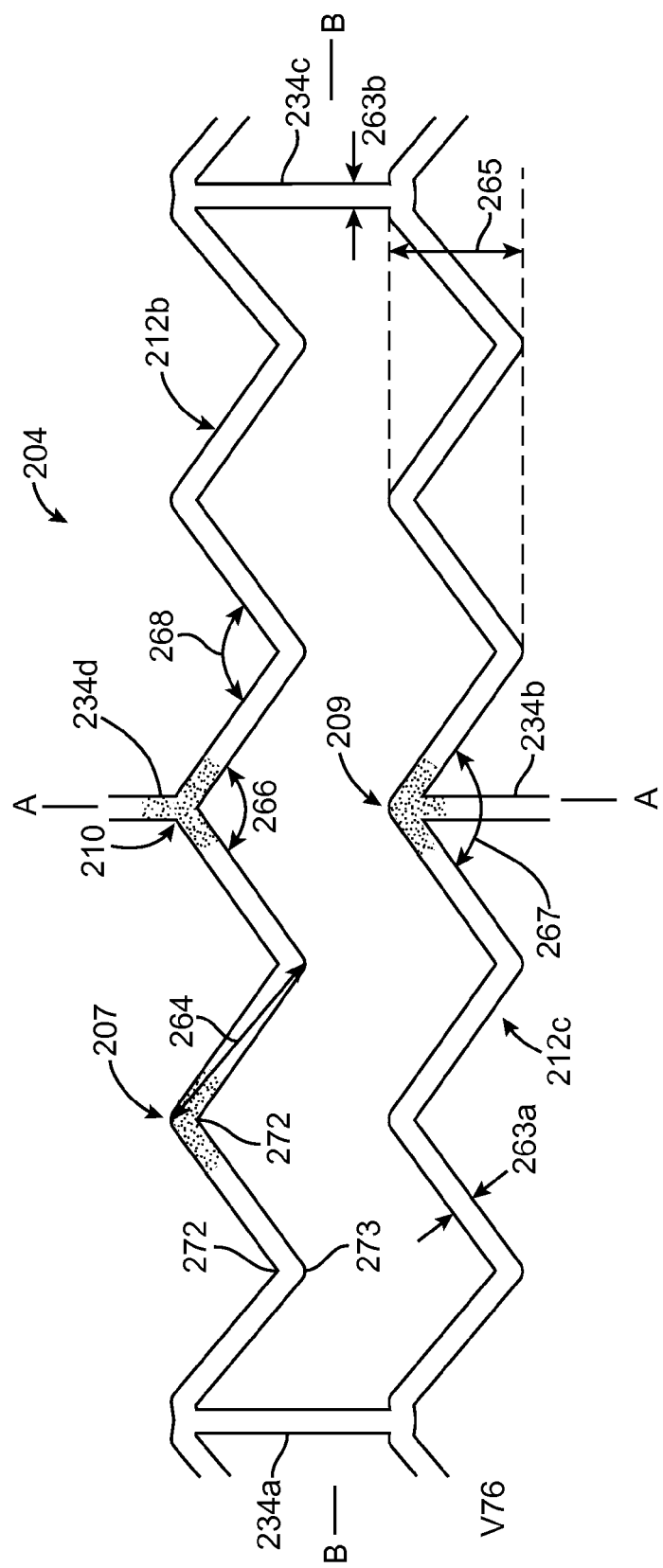
FIG. 5B shows the portion VB of the scaffold pattern of FIG. 2.

FIGS. 5A and 5B depict aspects of the repeating pattern of closed cell elements associated with each of the patterns 300 and 200, respectively. FIG. 5A shows the portion of pattern 300 bounded by the phantom box VA and FIG. 5B shows the portion of pattern 200 bounded by the phantom box VB. Therein are shown cell 304 and cell 204, respectively. In FIGS. 5A, 5B the vertical axis reference is indicated by the axis B-B and the longitudinal axis A-A. There are two such cells 204 formed by each pair of rings 212 in pattern 200, e.g., two cells 204 are formed by rings 212b and 212c and the links 234 connecting this ring pair, another two cells 204 are formed by rings 212a and 212b and the links connecting this ring pair, etc. Similarly, there are two cells 304 formed by rings 312b and 312c and the links 334 connecting this ring pair, another two cells 304 are formed by rings 312a and 312b and the links connecting this ring pair, etc.

Referring to FIG. 5A, the space 336 of cell 304 is bounded by the longitudinally spaced rings 312b and 312c portions shown, and the circumferentially spaced and parallel links 334a and 334c connecting rings 312b and 312c. Links 334b and 334d extend parallel to each other and connect the cell 304 to the right and left adjacent ring in FIG. 4, respectively. Link 334b connects to cell 304 at a W-crown 309. Link 334d connects to cell 304 at a Y-crown 310. A "W-crown" refers to a crown where the angle extending between a strut 330 and the link 334b at the crown 309 is an acute angle (less than 90 degrees). A "Y-crown" refers to a crown where the angle extending between a strut 330 and the link 334d at the crown 310 is an obtuse angle (greater than 90 degrees). The same definitions for Y-crown and W-crown also apply to the cell 204. There are eight unconnected or "U-crowns" 307 for cell 304, which may be understood as eight crowns devoid of a link 334 connected at the crown. There are always two U-crowns between a Y-crown or W-crown for the cell 304.

Additional aspects of the cell 304 of FIG. 5A include angles for the respective crowns 307, 309 and 310. Those angles are identified in FIG. 6A. For the scaffold having the pattern 300 the struts 330 have strut widths 363a, and the links 334 have link widths 363b. Each of the rings 312 has a ring height 365. The radii at the crowns are, in general, not equal to each other. The radii of the crowns are identified in FIG. 6A. Cell 304 of pattern 300 may be regarded as a symmetric cell, by virtue of it always having two U-crowns on each side of a W-crown and Y-crown as shown.

Referring to FIG. 5B, cell 204 is bounded by the portions of longitudinally spaced rings 212b and 212c as shown, and the circumferentially spaced and parallel links 234a and 234c connecting these rings. Links 234b and 234d connect the cell 204 to the right and left adjacent rings in FIG. 2, respectively. Link 234b connects to cell 204 at a W-crown 209. Link 234d connects to cell 204 at a Y-crown 210. There are four crowns 207 for cell 204, which may be understood as four crowns devoid of a link 234 connected at the crown. Cell 204 may also be regarded as a symmetric cell, by virtue of it always having one U-crown on each side of a W-crown and Y-crown as shown.

Additional aspects of the cell 204 of FIG. 5B include angles for the respective crowns 207, 209 and 210. Those angles are identified in FIG. 5B as angles 267, 269 and 268, respectively associated with crowns 207, 209 and 210. For the scaffold having the pattern 200 the struts 230 have strut widths 263a, crowns 207, 209, 210, and the links 234 have link widths 263b. Each of the rings 212 has a ring height 265. The radii of the crowns are identified in FIG. 5B as inner radii 272 and outer radii 273.

The V76 and V80 both have a symmetric cell design. A "symmetric" cell design (as shown in FIGS. 5A and 5B) has an equal number of U-crowns on each side of a W-crown or Y-crown. An example of an asymmetric cell design would be the V23 scaffold pattern, as described in US2011/0190871.

A significant difference between the V80 and V76 is that the V76 (as well as other designs, described below) has eight crowns and two links whereas the V80 design has twelve crowns and two links. Having more crowns and therefore shorter bar arms than other designs, the V80 has a higher density of struts. For example, a 60 mm V80 scaffold has 33 rings and a total of 396 ring struts/scaffold, which can be compared to a total of 216 ring struts (27 rings×8 struts per ring)/scaffold for the V76 design, and 200 ring struts/scaffold for the V59. In-vivo tests show that with a higher density of struts there is a lower late lumen loss for the V80.

Crimping of the scaffold, as detailed in U.S. application Ser. No. 13/194,162, includes heating the polymer material to a temperature less then, but near to the glass transition temperature of the polymer. In one embodiment the temperature of the scaffold during crimping is raised to about 5 to 10 degrees below the glass transition temperature for PLLA. When crimped to the final, crimped diameter, the crimping jaws are held at the final crimp diameter for final dwell period. This method for crimping a polymer scaffold having crush recovery is advantageous to reduce recoil when the crimp jaws are released. After the final dwell period, the scaffold is removed from the crimper and a constraining sheath is immediately placed over the scaffold to minimize recoil. Examples of such a sheath are described in US20120302955.

Testing of Scaffold Designs

TABLE 1 provides a summary of the characteristics of various scaffolds that were tested in in-vitro and in-vivo to evaluate and compare various performance characteristics, as described in FIGS. 7-22 and the description that follows.

TABLE 1 scaffold types

| Scaffold Type | Pattern | | | | |
|---|---|---|---|---|---|
| | Wall thickness (in) | Tube OD (mm) | Number of crowns | Links connecting adjacent rings | material |
| S-1, S-2 | see US application no. 13/252,121 (docket no. 104584.22) | | | | |
| V2 | .008 | 7 | 9 | 3 | PLLA |
| V23-008 | .008 | 7 | 9 | 3 | PLLA |
| V23-014 | .014 | 9 | 9 | 3 | PLLA |
| V59 | .011 | 8 | 8 | 4 | PLLA |
| V62 | .011 | 7 | 9 | 3 | PLLA |
| V76 | .011 | 7 | 8 | 2 | PLLA |
| V78 | .011 | 7 | 8 | 2 | PLLA |
| V79 | .011 | 7 | 8 | 2 | PLLA |
| V79 | .011 | 8 | 8 | 2 | PLLA-PCL (90/10) |
| V80 | .011 | 7 | 12 | 2 | PLLA |

FIGS. 7-16 show results from various in-vitro tests, which were used to compare the mechanical properties of the V76 and V62 scaffolds to the V59 scaffold (see US2011/0190871 for full description of the V59). These tests were directed towards determining the radial strength and/or stiffness, acute recoil, crush recovery, pinching stiffness, and fatigue or fracture of the scaffold after repeated loading of the scaffold.

The scaffolds were crimped to about a 0.085 in outer diameter (within the crimper head), sterilized by E-beam radiation, then expanded to 6.4 mm outer diameter using a 6.0 mm balloon prior to initiating the tests. The scaffold were made from PLLA and cut from a biaxial expanded tube using the process described earlier. Tests were conducted to assess the fracture toughness or number of discontinuous, cracked or broken struts appearing in the V59, V62 and V76 scaffolds under different test conditions.

Figure 7:
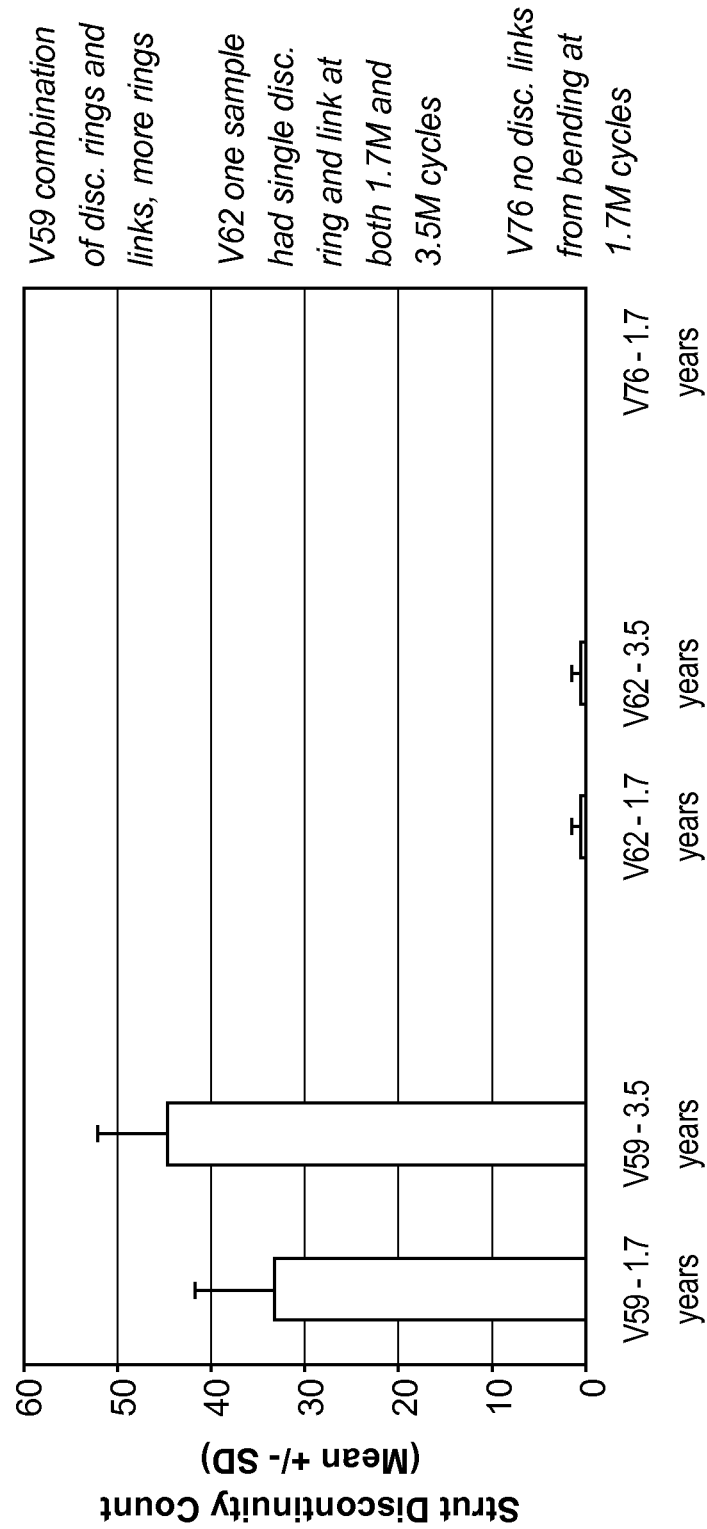
FIG. 7 compares results from a bending fatigue test among the V76, V62 and V59 scaffolds.

FIG. 7 compares results from a bending fatigue test between the V59, V62 and V76 scaffolds.

Figures 8, 9:
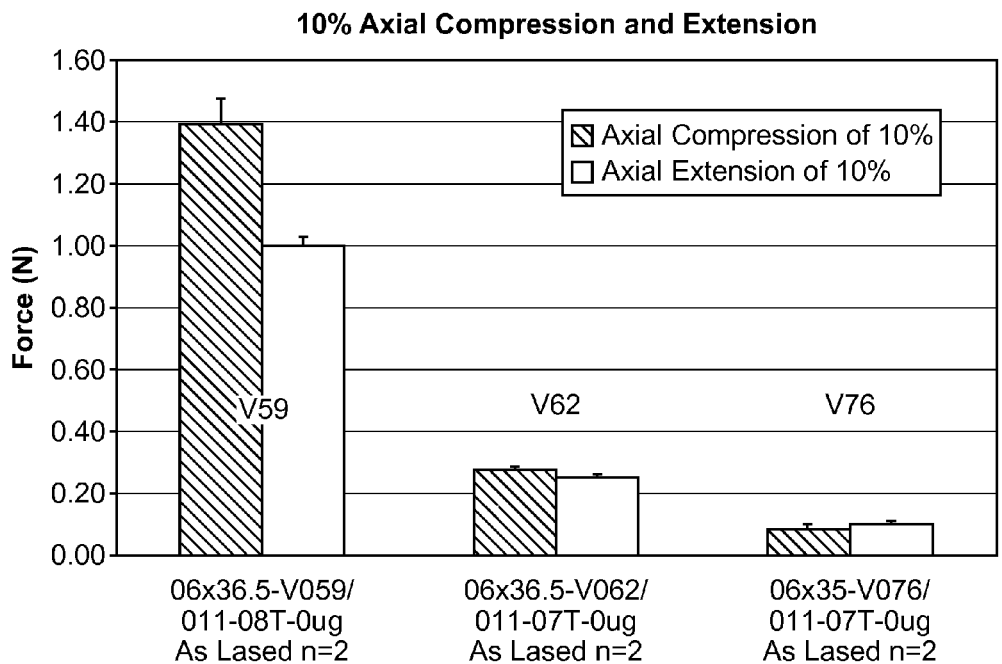
FIG. 8 compares the axial force among the V76, V62 and V59 scaffolds for a 10% static compression and extension.
FIG. 9 shows a mean and standard deviation fractures at crowns and links for the V76 scaffold for one month and six month simulations of axial loading of the V76 scaffold when contained within a model of the femoral artery.

FIG. 8 compares the axial force for a 10% static compression and extension of the V76 scaffold compared to the V59 and V62 scaffolds.

FIG. 9 is a table showing the mean and standard deviation fractures at crowns and links for the V76 scaffold for one month and six month simulations of axial loading of the V76 scaffold when implanted within the femoral artery. For these tests the V76 scaffold was subjected to a 7% axial compression and extension at 37 degrees Celsius within a loaded silicon tubing simulating axial loading of the femoral artery.

Figure 10:
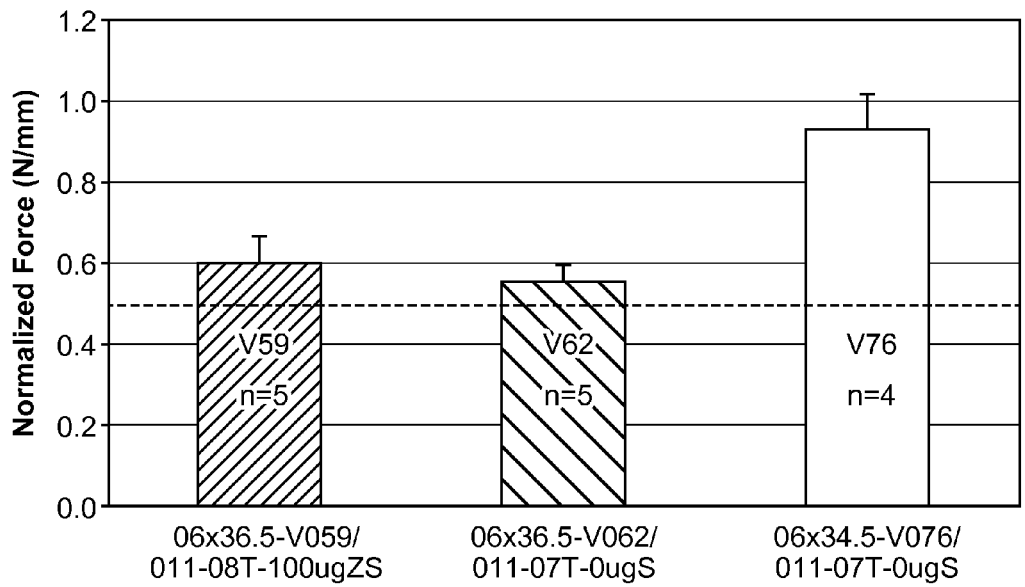
FIG. 10 compares the radial strength among the V76, V62 and V59 scaffolds.

FIG. 10 compares the radial strength of the V76 and V62 scaffolds to the V59 scaffold.

Figure 11:
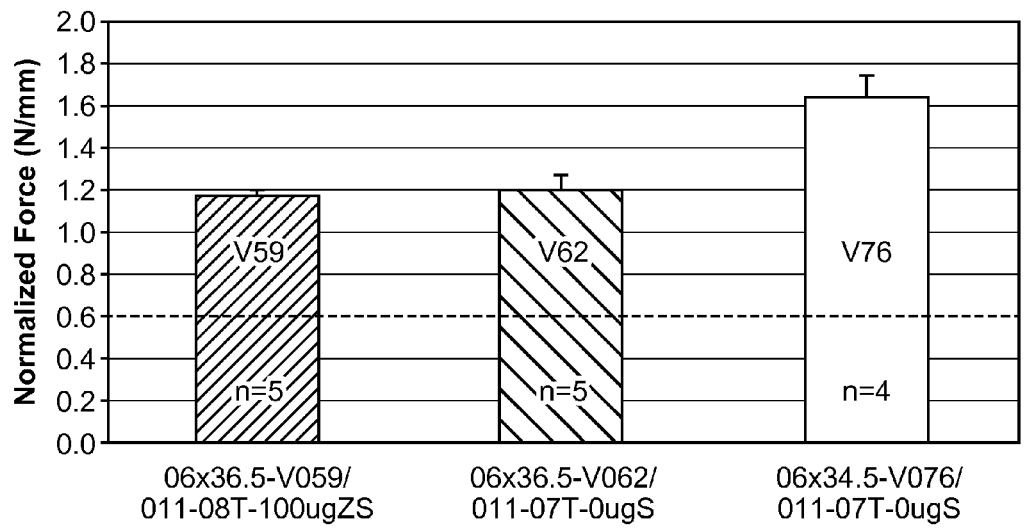
FIG. 11 compares the radial stiffness among the V76, V62 and V59 scaffolds.

FIG. 11 compares the radial stiffness of the V76 and V62 scaffolds to the V59 scaffold.

Figures 12, 13:
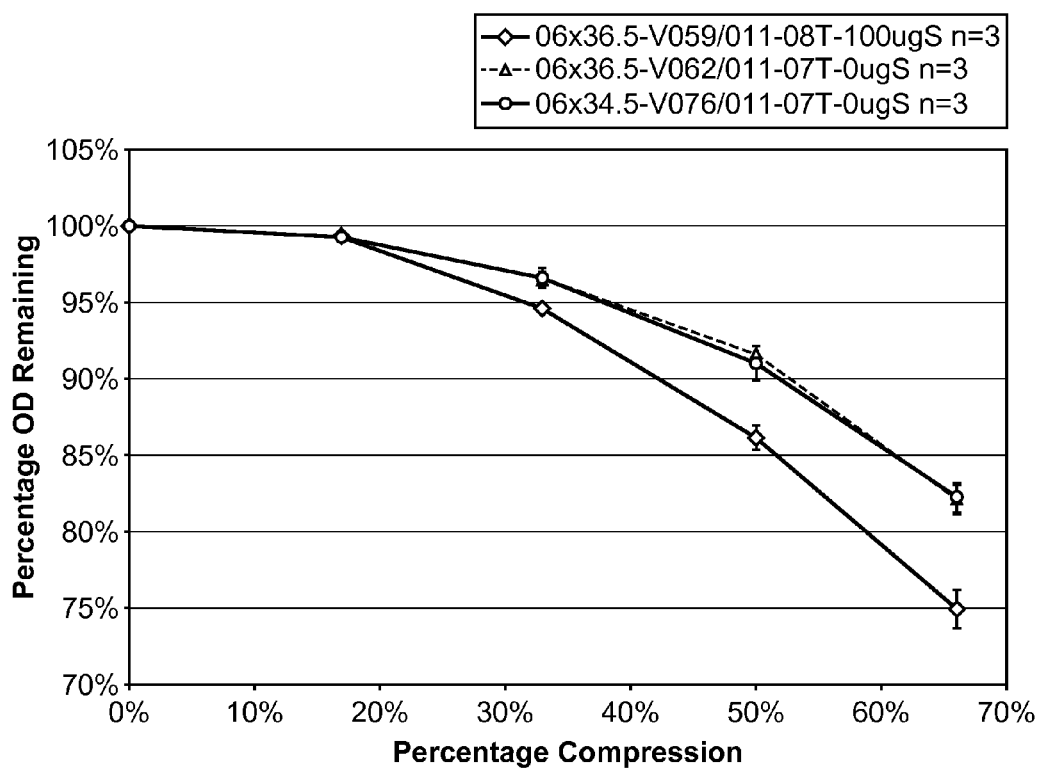
FIG. 12 compares the acute recoil of the V76 scaffold to the V59 and V62 scaffold, and the V2 scaffold described in WO2011094621.
FIG. 13 compares the crush-recovery among the V76, V62 and V59 scaffolds.

FIG. 12 compares the acute recoil of the V76 scaffold to the V59, V2 (as described in US2011/0190871) and V62 scaffolds.

FIG. 13 compares the crush-recovery of the V76 scaffold to the V59 scaffold and V62 scaffolds.

Figure 14:
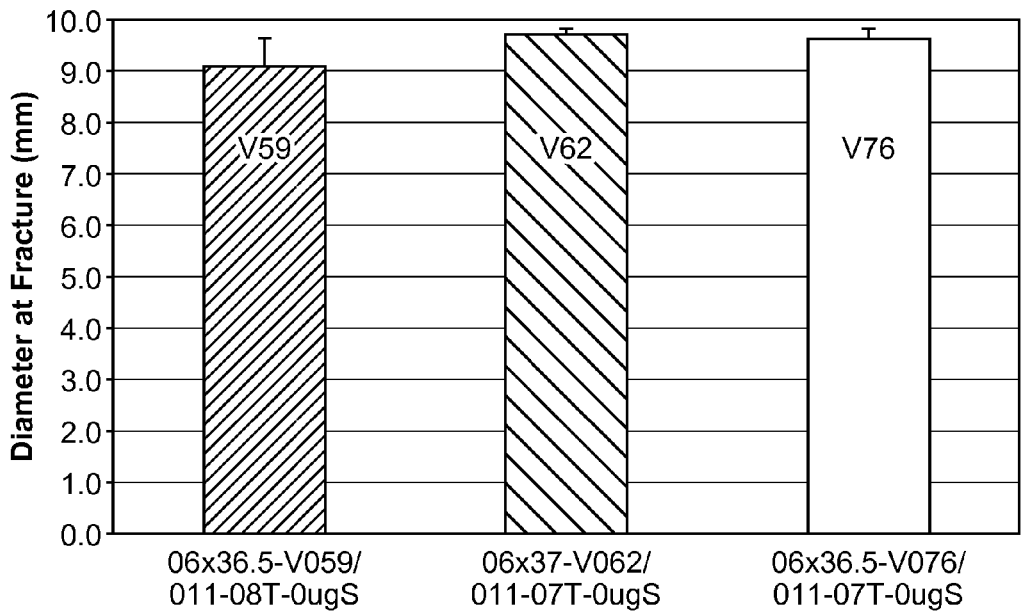
FIG. 14 compares the deploy-to-fracture among the V76, V62 and V59 scaffolds. This plot shows that the V76 begins to develop critical fractures at a higher diameter than the V59.
Figure 15:
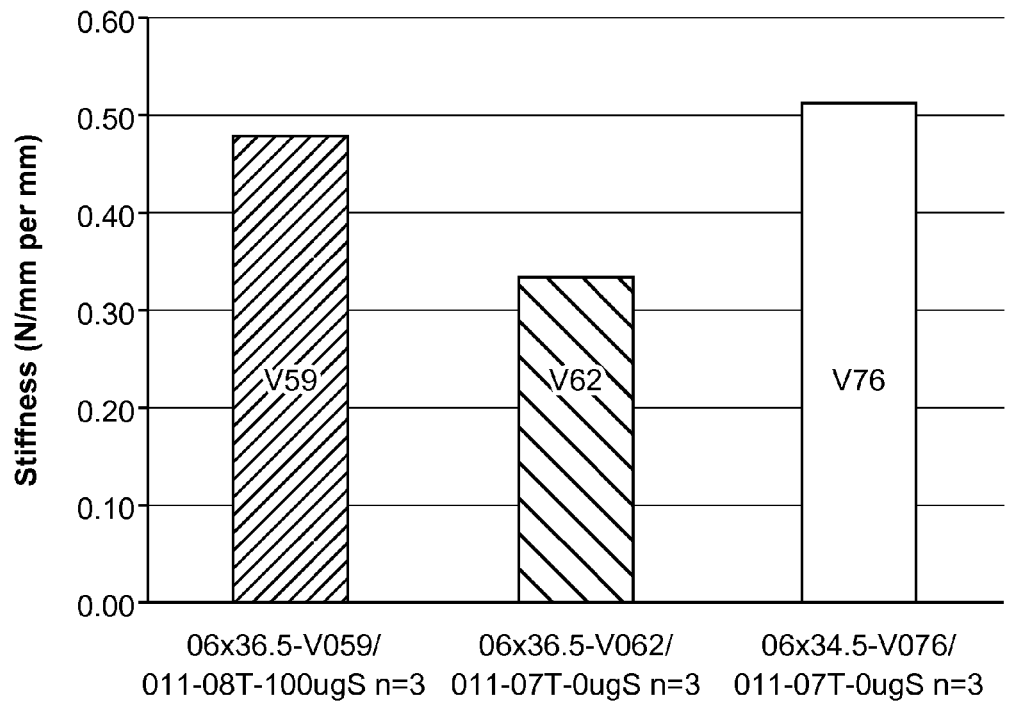
FIG. 15 compares the pinching stiffness among the V76, V62 and V59 scaffolds.

FIG. 14 compares the deploy-to-fracture of the V76 scaffold to the V59 scaffold and V62 scaffolds. This plot shows that the V76 begins to develop critical fractures at a higher diameter than the V59. FIG. 15 compares the pinching stiffness of the V76 scaffold to the V59 scaffold and V62 scaffolds.

Figure 16:
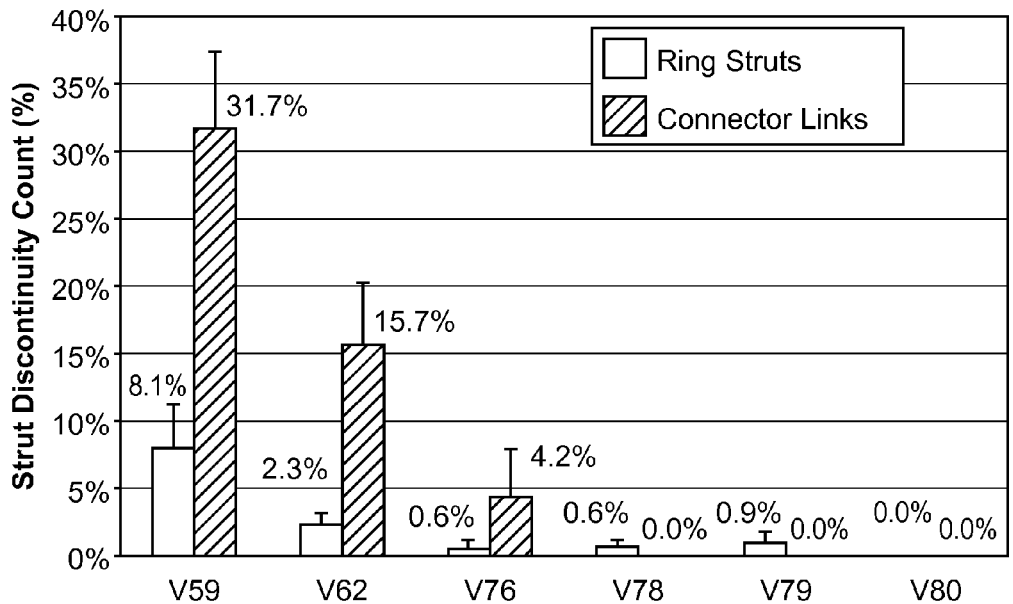
FIG. 16 compares the percentage of discontinuities, fractures or failures of struts and links among several scaffold designs having different numbers of crowns and/or links connecting ring structures.

FIG. 16 shows the total percentage of discontinuity (cracked or broken struts and links) for the V59, V62, V76, V78, V79 and V80 scaffolds after 500,000 cycles of 7% axial compression of the scaffold (equivalent to 6-month walking).

In-Vivo Testing

FIGS. 17-20 compares minimum lumen diameter (MLD) or late loss and percentage of stenosis following a 28 day implant for each of the scaffold in TABLE 1. Each scaffold was implanted into the iliofemoral artery of a healthy porcine model and after 28 days explants were obtained in order to evaluate and compare the effectiveness of the polymer scaffolds in maintaining vascular patency. The implanted scaffolds were subject to various degrees of hip extension and flexion by the swine, which is believed to impose about 90 degrees bending, and about 3-15% axial compression of the implanted scaffold during a maximum hip and knee flexion.

The scaffold were crimped to about a 0.085 in outer diameter (within the crimper head), sterilized by E-beam radiation, introduced into the animal model using standard procedures, then expanded within the artery to a 6.4 mm outer diameter using a 6.0 mm balloon. The scaffold were made from PLLA (exc. V79 PLLA-PCL) and cut from a biaxial expanded tube using the process described earlier.

The data in FIGS. 17-20 were obtained using Quantitative Vascular Analysis (QVA) to determine the MLD and stenosis %. The number "n" in the figures represents the number of explants that were used to arrive at the mean and standard deviation values provide in FIGS. 17-20.

Figure 17:
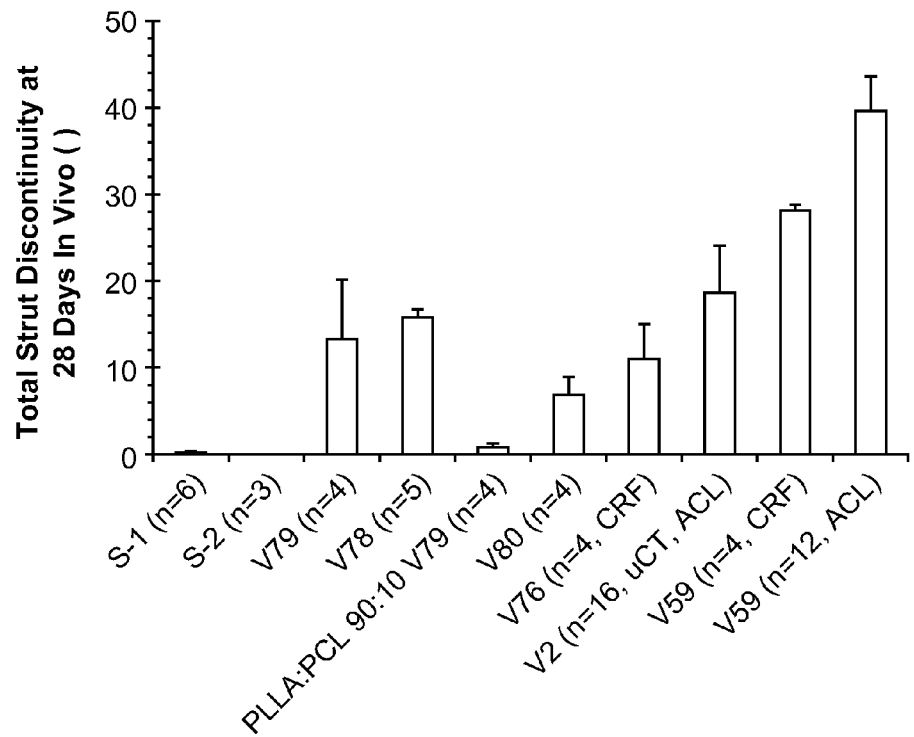
FIG. 17 counts the total number of discontinuities, fractures or failures of struts and links among the several scaffold designs from FIG. 17.

FIG. 17 counts the total number of strut discontinuities found in the explants for the V59, V62, V76, V79 and V80 scaffolds.

Figure 18:
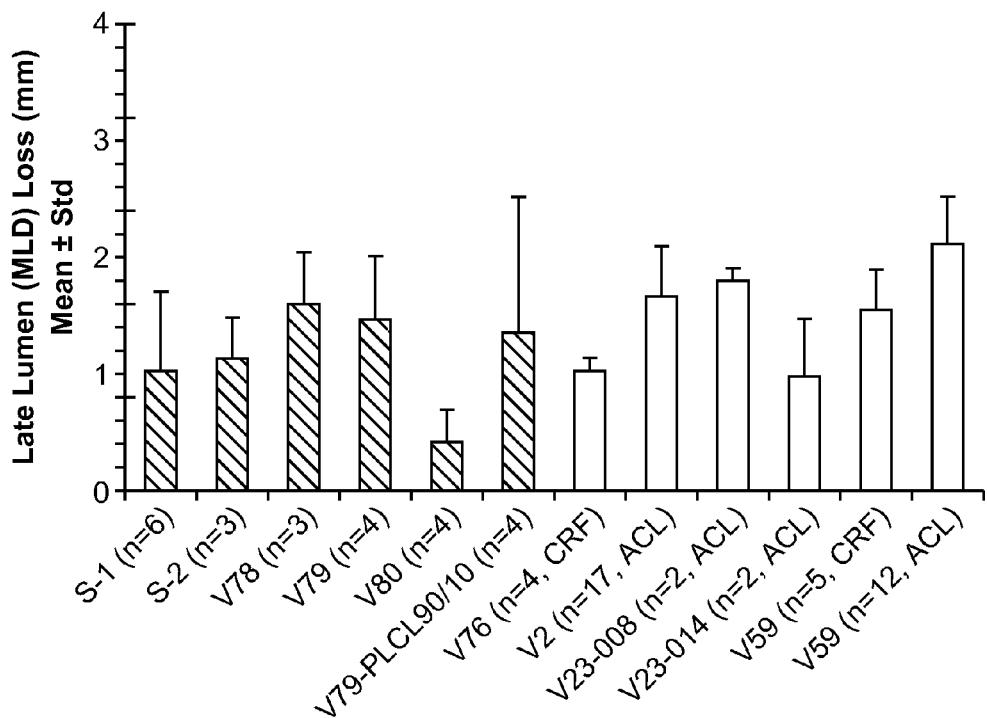
FIG. 18 compares the in-vivo late lumen loss among several scaffold designs after 28 days implantation.

FIG. 18 compares the late lumen loss or minimum lumen diameter (MLD) in the explants for the V59, V62, V76, V79 and V80 scaffolds.

Figure 19:
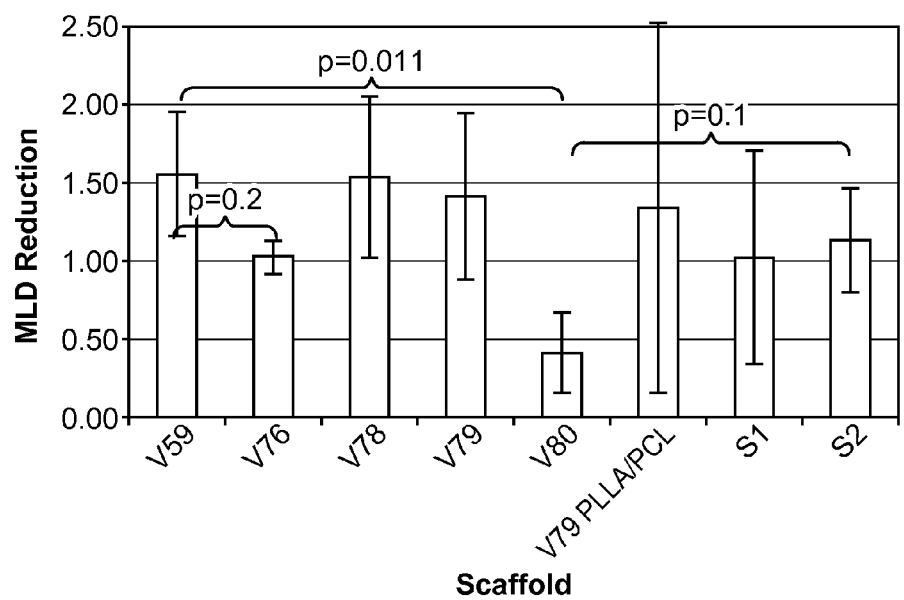
FIG. 19 provides statistical significance values (t-test) for the late lumen loss in FIG. 18.

FIG. 19 shows late lumen loss from FIG. 18 with statistical significance indicated between scaffolds. There is a p value of 0.011 (t-test) for the V80 scaffold data compared to the V59 scaffold data. Table 2, below, provides a summary of characteristics of the scaffolds. "ACL" and "CRF" indicate different locations for the in-vivo tests.

Referring to FIG. 16, the high number of crests provides the V80 scaffolds with unique flexibility and as a result is more fracture resistant than the other scaffolds when axial fatigue properties are evaluated using 7% compression through 500,000 cycles (equivalent to 6-month walking). The low fracture rate is also well translated and shows good correlation with in-vivo testing, as demonstrated in FIG. 18.

Because the V80 scaffold has more struts/scaffold-length than the other scaffolds, the struts need to be less wide and as a result the radial strength of the V80 scaffold is significantly lower than other two-link scaffolds (V76-V79).

Radial strength and stiffness are sometimes thought of as synonymous to scaffolding properties. According to this view, the V80 design would therefore appear to have a poor ability to maintain patency as compared to the other scaffolds. However, as seen in FIG. 18 the V80 scaffold shows a significantly lower late loss than the other more radially stiff scaffolds, even where the fracture percentages and/or rates are similar, e.g., V79 compared with V80. As shown in FIG. 19 the lower late loss shows statistical significance at 28 days relative to the other scaffold designs.

While not wishing to be tied to any particular theory, the explanation for why the V80 design shows significantly lower late loss is believed to lie in the higher number of, or density of struts. With a greater number of struts the V80 provides more scaffolding (higher surface area and more support). In particular, when a strut is fracturing there is still significant support to push back the vessel. This aspect of the V80 may be understood in the following manner. For an equal number of fractures, there is a lower percentage of non-functioning strut-crown structures to the total number of strut-crown structures. Thus, while there may be an equal number of fractures as in other designs, the V80 is capable of providing a better or more consistent scaffolding over the vessel luminal surface because it has a larger number of intact crown-strut structures for every failed crown-strut structure.

Figure 20:
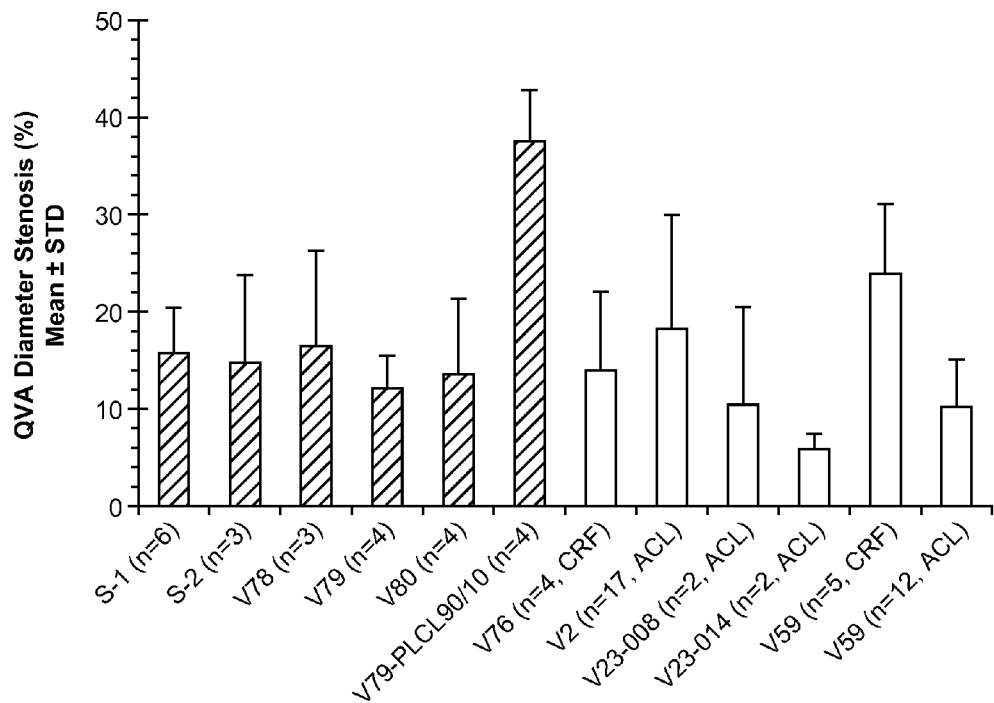
FIG. 20 compares the percentage diameter stenosis 28 days following implantation for different scaffolds.

FIG. 20 shows that the V23-014 scaffold, which has a lower number of crowns but a higher wall thickness, produced a lower percentage of stenosis than the V80. This may be explained by an increase in the fatigue life of the scaffold struts (i.e., fewer fractures) since the thicker wall lowers the average stress for a strut for the same loading conditions.

TABLE 2 performance characteristics for scaffold types in TABLE 1

Figure 21:
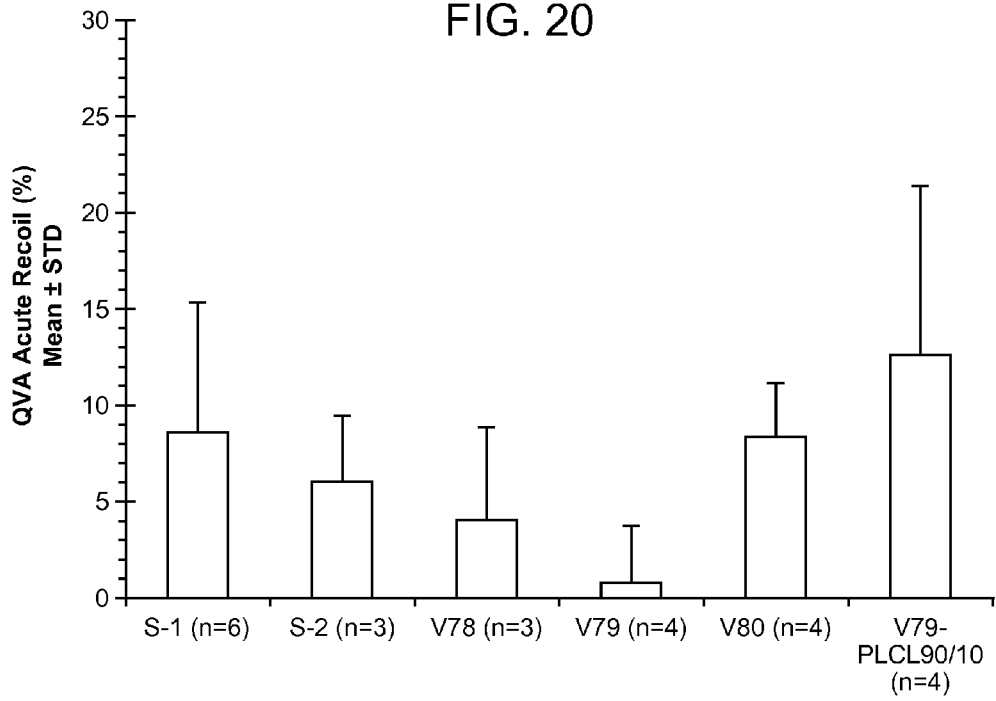
FIG. 21 compares the acute recoil percentage for several different scaffolds.
Figure 22:
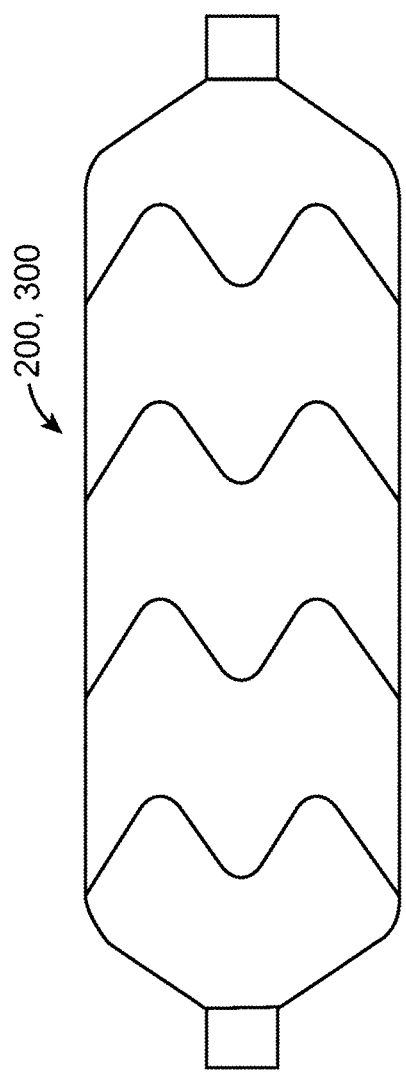
FIG. 22 shows a scaffold crimped to a balloon.

| Scaffold Type | Stenosis (28 days) (%) FIG. 21 | Late Lumen loss (28 days) (mm) FIG. 19 | Axial Fatigue % (6 months) struts FIG. 17 | Axial Fatigue % (6 months) links FIG. 17 | Stiffness (N/mm) FIG. 16 | In vivo % fracture (28 days) FIG. 18 | Acute recoil (%) FIGS. 13 and 22 |
|---|---|---|---|---|---|---|---|
| V2 | 18 (ACL) | 1.6 (ACL) | — | — | 0.15* | 19 | 2.5 |
| V23-008 | 10 (ACL) | 1.8 (ACL) | — | — | 0.20* | 18 | — |
| V23-014 | 6 (ACL) | 1.0 (ACL) | — | — | 0.39* | — | — |
| V59 | 24 (CRF)/ 10 (ACL) | 1.5 (CRF)/ 2.1 (ACL) | 8.1 | 31.7 | 0.54* | 38 (ACL)/ 28 (CRF) | 3.2 |
| V62 | — | — | 2.3 | 15.7 | 0.34 | — | 3.8 |
| V76 | 13 (CRF) | 1.0 (CRF) | 0.58 | 4.23 | 0.50 | 11 | 3.3 |
| V78 | 16 | 1.6 | 0.60 | 0.00 | — | 16 | 4 |
| V79 | 12 | 1.4 | 0.89 | 0.00 | — | 13 | 1 |
| V79 (PLLA-PCL) | 37 | 1.3 | — | — | — | 1 | 13 |
| V80 | 12 | 0.4 | 0.00 | 0.00 | — | 8 | 8 |

FIG. 21 shows acute recoil for the V78, V79, V80 and V79 scaffolds.

Below the Knee (BKN) Applications

In one embodiment there is a scaffold characterized as flexible, long and bioresorbable for below the knee (BTK) applications.

Critical limb ischemia (CLI) represents the most severe clinical manifestation of peripheral disease (PAD). CLI is a chronic disease process that ultimately leads to limb loss left untreated and perhaps death from development of sepsis. Approximately 30% of lesions of CLI cases are confined to the BTK arteries and most procedures include more proximal femoral and popliteal segments. Disease in the tibial arteries tends to be diffuse and is usually associated with long segment stenoses and occlusions. The small caliber of the arteries, heavy calcification, slow of distal beds, and poor run-off vessels represent significant challenges to endovascular interventions. There are many angioplasty technologies such as BTK balloon angioplasty with a reasonably high technical success, Endovascular cryoplasty (Boston Scientific), Cutting balloon angioplasty, Drug-eluting balloons, Excimer laser atherectomy, rotational atherectomy are few of these techniques to name.

Restenosis after PTA remains a problem that significantly affects mid- and long term outcomes. However, stents are not widely used in BTK vessels compared to ileofemoral diseases. The main reason is the small caliber and slow flow in these vessels increase the risk of stent thrombosis and intimal hyperplasia. The traditional indications for stenting are for bail-out after failed or unsuccessful angioplasty, such as flow limiting dissection or elastic recoil. A meta-analysis of 640 patients showed that BTK stent implantation after failed or unsuccessful balloon angioplasty was associated with favorable clinical results in patients with CLI. With advances in scaffold technology, there is increasing evidence to support primary scaffolding in CLI with BTK disease. Balloon expandable bare metal stents and DES self-expanding nitinol stents have been used. In either of cases, if damage is done due to an external force or there is a need to implant another stent in the distal position of the limb, the patient needs to go under surgery or lose the limb.

As an example of a scaffolding for BTK, polylactic acid tubes were expanded to 3.5 mm in OD and cut into 100 mm in length pieces. The tubes were laser cut. The scaffold design for "BTK_01×100 mm" is the same as V76, V78, and V79 (i.e. two link, in phase, symmetric, eight crowns). The design concept is symmetric, meaning there is an even number of U-crowns on either side of the linked W-V (one or two). The concept as shown has one U-crown on either side. The BTK_01×100 mm may alternatively adopt the V80 pattern. The advantages of these designs are that they have better and more symmetric deformation during axial loading.

Currently the ABSORB BTK uses a 'non-symmetric" 28 mm length stent. The "BTK_01×100 mm" design is longer (100 mm as shown). As compared to other scaffold designs (TABLE 3):

TABLE 3

BTK scaffold ("BTK_01 × 100 mm") as compared to V79 and ABSORB BTK

|  | V79 | ABSORB BTK | BTK_01 × 100 mm |
|---|---|---|---|
| Design | 8C-2L | 6C-3L | 8C-2L |
| Length (mm) | NA | 28 | 100 |
| Tubing (mm) | 7.0 × 0.279 | 3.5 × 0.152 | 3.5 × 0.152 |
| BA Length (mm) | 1.74 | 0.86 | 0.78 |
| 'Strut Width (mm) | 0.300 | 0.165 | 0.130 |
| Link Width (mm) | 0.300 | 0.127 | 0.110 |
| Inner Radius (mm) | 0.18 | 0.31/0.07 | 0.10 |
| Theor. Min Crimp (mm) | 02.28 | 1.06 | 1.04 |
| Theor. Max Exp (mm) | 9.60 | 3.87 | 4.25 |

BTK_01×100 mm, although similar in concept to V79 (8C-2L symmetric) is cut from the same tubing as ABSORB BTK and is designed for similar artery diameters. BTK_01× 100 mm has a similar theoretical min crimp and max expansion diameters. A slightly larger max expansion diameter is given to accommodate for tapering along a longer vessel length.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device, comprising:
   a scaffold crimped to a balloon;
   the scaffold forming a network of rings interconnected by links, including
   12 crests and 12 troughs per ring,
   each ring having a plurality of U crowns, Y crowns and W crowns,
   the rings including a first ring, a second ring adjacent the first ring, a third ring adjacent the second ring, and a fourth ring adjacent the third ring,
   the first ring is connected to the second ring by at most two links, each of which being connected to the first ring at a W crown and the second ring at a Y crown and such that there are an equal number of U crowns on each side of the W crown of the first ring and each side of the Y crown of the second ring,
   the second ring is connected to the third ring by at most two links, each of which being connected to the second ring at a W crown and the third ring at a Y crown and such that there are an equal number of U crowns on each side of the W crown of the second ring and each side of the Y crown of the third ring,
   the third ring is connected to the fourth ring by at most two links, each of which being connected to the third ring at a W crown and the fourth ring at a Y crown and such that there are an equal number of U crowns on each side of the W crown of the third ring and each side of the Y crown of the fourth ring, and
   wherein the scaffold has a wall thickness of between 0.203 mm and 0.356 mm and a pre-crimp diameter between 7 mm and 9 mm, and
   wherein
   the balloon has a nominal inflation diameter,
   the scaffold attains a plastically deformed state when the balloon is inflated to the nominal inflation diameter, whereupon the scaffold has an expanded diameter, and the scaffold attains about 80% of the expanded diameter after being crushed to over 50% of the expanded diameter.

2. The device of claim 1, where the scaffold is made from poly (L-lactide (PLLA) or a copolymer of PLLA and polycaprolactone (PCL).

3. The device of claim 1, wherein the balloon has a nominal inflation diameter of 6 mm.

4. The device of claim 1, wherein an aspect ratio (AR) of a strut width of a strut of a ring to the wall thickness is about 0.7.

5. The device of claim 1, wherein an aspect ratio (AR) of a link width to the wall thickness is about 0.7.

6. The device of claim 1, wherein the scaffold is characterized by
   (1) radially aligned polymer chains resulting from a biaxial expansion of a precursor tube that was formed into the scaffold, and
   (2) the scaffold was crimped from the pre-crimp diameter to a diameter that is at least 2-3 times reduced from the pre-crimp diameter.

7. The device of claim 6, wherein the scaffold is made from PLLA.

8. The device of claim 6, wherein the polymer chains of the scaffold are aligned in a radial direction resulting from a radial draw percentage of between about 400% and 450%.

9. The device of claim 1, wherein the scaffold attains over 90% of its diameter after being crushed to 50% of its diameter.

10. The device of claim 1, wherein the scaffold is formed from a biaxially expanded polymer tube.

11. The device of claim 10, wherein the scaffold has a semi-crystalline structure resulting from a process where an extruded precursor tube is radially expanded using a radial draw ratio of over 400% to produce the radially expanded tube from which the scaffold was made.

12. The medical device of claim 1, wherein each of the links has a longitudinal axis and extends parallel to a longitudinal axis of the scaffold, and wherein each of the links connecting the first ring to the second ring is co-linear with a respective one of the links connecting the third ring to the fourth ring.

13. A medical device, comprising:
a scaffold crimped to a balloon having a nominal inflation diameter;
the scaffold having a longitudinal axis and forming a network of rings interconnected by links, including
   8 to 12 crests and 8 to 12 troughs, respectively per ring,
   each ring having a plurality of U crowns, Y crowns and W crowns,
   the rings including a first ring, a second ring adjacent the first ring, a third ring adjacent the second ring, and a fourth ring adjacent the third ring,
   the first ring is connected to the second ring by at most two links, each of which being connected to the first ring at a W crown and the second ring at a Y crown and such that there are an equal number of U crowns on each side of the W crown of the first ring and each side of the Y crown of the second ring,
   the second ring is connected to the third ring by at most two links, each of which being connected to the second ring at a W crown and the third ring at a Y crown and such that there are an equal number of U crowns on each side of the W crown of the second ring and each side of the Y crown of the third ring, and
   the third ring is connected to the fourth ring by at most two links, each of which being connected to the third ring at a W crown and the fourth ring at a Y crown and such that there are an equal number of U crowns on each side of the W crown of the third ring and each side of the Y crown of the fourth ring,
   wherein each of the links has a longitudinal axis and extends parallel to the longitudinal axis of the scaffold, and wherein each of the links connecting the first ring to the second ring is co-linear with a respective one of the links connecting the third ring to the fourth ring, and
   wherein the scaffold further includes
      a wall thickness of between 0.203 mm and 0.356 mm,
      a pre-crimp diameter of between 7 mm and 9 mm, and
      a pre-crimp diameter greater than or equal to the nominal inflation diameter.

* * * * *